(12) United States Patent
Shimada et al.

(10) Patent No.: US 11,642,061 B2
(45) Date of Patent: May 9, 2023

(54) INTRALUMINAL MICRONEUROGRAPHY DENERVATION PROBE WITH RADIO FREQUENCY ABLATION

(71) Applicant: RECOR MEDICAL, INC., Palo Alto, CA (US)

(72) Inventors: Jin Shimada, White Bear Lake, MN (US); Harry A. Puryear, Shoreview, MN (US)

(73) Assignee: ReCor Medical, Inc., Palo Alto, CA (US)

( * ) Notice: Subject to any disclaimer, the term of this patent is extended or adjusted under 35 U.S.C. 154(b) by 767 days.

(21) Appl. No.: 16/517,180

(22) Filed: Jul. 19, 2019

(65) Prior Publication Data

US 2020/0077907 A1   Mar. 12, 2020

Related U.S. Application Data

(63) Continuation of application No. 15/299,694, filed on Oct. 21, 2016, now abandoned, which is a
(Continued)

(51) Int. Cl.
*A61B 5/24* (2021.01)
*A61B 5/00* (2006.01)
(Continued)

(52) U.S. Cl.
CPC ............ *A61B 5/24* (2021.01); *A61B 5/201* (2013.01); *A61B 5/4836* (2013.01); *A61B 5/725* (2013.01);
(Continued)

(58) Field of Classification Search
CPC ....... A61B 5/201; A61B 5/279; A61B 5/6857; A61B 5/6859
See application file for complete search history.

(56) References Cited

U.S. PATENT DOCUMENTS 4,643,186 A * 2/1987 Rosen ................... A61B 18/18
                                                            607/156
4,709,698 A    12/1987 Johnston et al.
(Continued)

OTHER PUBLICATIONS

"U.S. Appl. No. 15/943,354, Restriction Requirement dated Nov. 20, 2019", 8 pages.
(Continued)

*Primary Examiner* — Eun Hwa Kim
(74) *Attorney, Agent, or Firm* — Theresa Ann Raymer

(57) ABSTRACT

An intraluminal microneurography probe has a probe body configured to be introduced into an artery near an organ of a body without preventing the flow of blood through the artery. An expandable sense electrode and an expandable stimulation electrode are fixed to the probe body at one end of each electrode such that movement of the other end toward the fixed end causes the sense electrode to expand from the probe body toward a wall of the artery. A ground electrode is configured to couple to the body, and a plurality of electrical connections are operable to electrically couple the electrodes to electrical circuitry. The sense electrode is operable to measure sympathetic nerve activity in response to excitation of the stimulation electrode. A radio frequency ablation element is located between the expandable sense electrode and expandable stimulation electrode, and is operable to ablate nerves proximate to the artery.

28 Claims, 9 Drawing Sheets

Related U.S. Application Data continuation of application No. 15/204,349, filed on Jul. 7, 2016, now abandoned.

(60) Provisional application No. 62/198,382, filed on Jul. 29, 2015.

(51) Int. Cl.
  *A61B 18/14* (2006.01)
  *A61B 5/20* (2006.01)
  *A61N 1/18* (2006.01)
  *A61B 18/18* (2006.01)
  A61B 18/00 (2006.01)
  A61B 18/12 (2006.01)
  A61B 18/16 (2006.01)

(52) U.S. Cl.
  CPC ...... *A61B 18/1492* (2013.01); *A61B 18/1815* (2013.01); *A61N 1/18* (2013.01); A61B 2018/00023 (2013.01); A61B 2018/00267 (2013.01); A61B 2018/00404 (2013.01); A61B 2018/00434 (2013.01); A61B 2018/00511 (2013.01); A61B 2018/00577 (2013.01); A61B 2018/00839 (2013.01); A61B 2018/126 (2013.01); A61B 2018/1253 (2013.01); A61B 2018/1407 (2013.01); A61B 2018/1467 (2013.01); A61B 2018/162 (2013.01); A61B 2018/1861 (2013.01); A61B 2562/028 (2013.01)

(56) References Cited

U.S. PATENT DOCUMENTS

| | | | |
|---|---|---|---|
| 5,657,755 | A | 8/1997 | Desai |
| 6,529,756 | B1 * | 3/2003 | Phan ............... A61B 18/1492 606/49 |
| 6,837,886 | B2 * | 1/2005 | Collins ............ A61B 18/1492 606/41 |
| 8,447,414 | B2 | 5/2013 | Johnson et al. |
| 8,483,831 | B1 | 7/2013 | Hlavka et al. |
| 8,932,289 | B2 | 1/2015 | Mayse et al. |
| 9,333,035 | B2 | 5/2016 | Rudie |
| 9,649,064 | B2 | 5/2017 | Toth et al. |
| 9,730,639 | B2 | 8/2017 | Toth et al. |
| 9,956,034 | B2 | 5/2018 | Toth et al. |
| 9,999,463 | B2 | 6/2018 | Puryear et al. |
| 10,004,458 | B2 | 6/2018 | Toth et al. |
| 2001/0023365 | A1 | 9/2001 | Medhkour et al. |
| 2002/0173724 | A1 | 11/2002 | Dorando et al. |
| 2003/0074039 | A1 | 4/2003 | Puskas |
| 2004/0097819 | A1 | 5/2004 | Duarte |
| 2004/0122494 | A1 | 6/2004 | Eggers et al. |
| 2005/0159738 | A1 * | 7/2005 | Visram ............ A61B 18/1492 606/41 |
| 2006/0217772 | A1 | 9/2006 | Libbus et al. |
| 2006/0235286 | A1 | 10/2006 | Stone et al. |
| 2007/0106292 | A1 | 5/2007 | Kaplan et al. |
| 2007/0265687 | A1 * | 11/2007 | Deem ................ A61B 8/12 607/72 |
| 2009/0234407 | A1 | 9/2009 | Hastings et al. |
| 2009/0248005 | A1 | 10/2009 | Rusin et al. |
| 2012/0265198 | A1 | 10/2012 | Crow et al. |
| 2012/0296329 | A1 * | 11/2012 | Ng ................... A61B 5/0215 606/41 |
| 2013/0085489 | A1 | 4/2013 | Fain et al. |
| 2013/0096550 | A1 | 4/2013 | Hill |
| 2013/0131743 | A1 | 5/2013 | Yamasaki et al. |
| 2013/0274614 | A1 | 10/2013 | Shimada et al. |
| 2013/0289369 | A1 | 10/2013 | Margolis |
| 2014/0275924 | A1 | 9/2014 | Min et al. |
| 2014/0288551 | A1 | 9/2014 | Bharmi et al. |
| 2014/0288616 | A1 | 9/2014 | Rawat et al. |
| 2015/0289931 | A1 | 10/2015 | Puryear et al. |
| 2017/0003531 | A1 | 2/2017 | Shimada et al. |
| 2017/0027460 | A1 | 2/2017 | Shimada et al. |
| 2018/0064359 | A1 * | 3/2018 | Pranaitis ............ A61B 5/25 |
| 2018/0221087 | A1 | 8/2018 | Puryear et al. |
| 2018/0280082 | A1 | 10/2018 | Puryear et al. |

OTHER PUBLICATIONS

"U.S. Appl. No. 15/943,354, Response filed Dec. 19, 2019 to Restriction Requirement dated Nov. 20, 2019", 8 pages.
"U.S. Appl. No. 15/943,354, Non Final Office Action dated Jan. 13, 2020", 6 pages.
"U.S. Appl. No. 15/996,978, Restriction Requirement dated Feb. 7, 2020", 7 pages.
"U.S. Appl. No. 14/683,966, 312 Amendment filed Mar. 13, 2018", 10 pgs.
"U.S. Appl. No. 14/683,966, Corrected Notice of Allowance dated May 22, 2018", 4 pgs.
"U.S. Appl. No. 14/683,966, Non Final Office Action dated Jun. 12, 2017", 14 pgs.
"U.S. Appl. No. 14/683,966, Notice of Allowance dated Jan. 31, 2018", 8 pgs.
"U.S. Appl. No. 14/683,966, PTO Response to Rule 312 Communication dated Mar. 29, 2018", 2 pgs.
"U.S. Appl. No. 14/683,966, Response filed Nov. 10, 2017 to Non Final Office Action dated Jun. 12, 2017", 13 pgs.
"U.S. Appl. No. 15/204,349, Advisory Action dated Jul. 9, 2019", 5 pgs.
"U.S. Appl. No. 15/204,349, Final Office Action dated Apr. 22, 2019", 16 pgs.
"U.S. Appl. No. 15/204,349, Non Final Office Action dated Nov. 27, 2018", 14 pgs.
"U.S. Appl. No. 15/204,349, Preliminary Amendment filed Nov. 30, 2016", 3 pgs.
"U.S. Appl. No. 15/204,349, Response filed Feb. 27, 2019 to Non Final Office Action dated Nov. 27, 2018", 10 pgs.
"U.S. Appl. No. 15/204,349, Response filed Jun. 5, 2018 to Restriction Requirement dated May 17, 2018", 7 pgs.
"U.S. Appl. No. 15/204,349, Response filed Jun. 24, 2019 to Final Office Action dated Apr. 22, 2019", 12 pgs.
"U.S. Appl. No. 15/204,349, Restriction Requirement dated May 17, 2018", 7 pgs.
"U.S. Appl. No. 15/299,694, Advisory Action dated Jul. 9, 2019", 5 pgs.
"U.S. Appl. No. 15/299,694, Final Office Action dated Apr. 22, 2019", 16 pgs.
"U.S. Appl. No. 15/299,694, Non Final Office Action dated Nov. 27, 2018", 15 pgs.
"U.S. Appl. No. 15/299,694, Response filed Feb. 27, 2019 to Non Final Office Action dated Nov. 27, 2018", 10 pgs.
"U.S. Appl. No. 15/299,694, Response filed Jun. 24, 2019 to Final Office Action dated Apr. 22, 2019", 11 pgs.
"U.S. Appl. No. 15/299,694, Response filed Oct. 8, 2018 to Restriction Requirement dated Aug. 6, 2018", 7 pgs.
"U.S. Appl. No. 15/299,694, Restriction Requirement dated Aug. 6, 2018", 6 pgs.
"U.S. Appl. No. 15/943,354, Preliminary Amendment filed Apr. 3, 2018", 9 pgs.
"U.S. Appl. No. 15/996,978, Preliminary Amendment filed Jun. 5, 2018", 11 pgs.
Accornero, Neri, et al., "Selective Activation of Peripheral Nerve Fibre Groups of Different Diameter by Triangular Shaped Stimulus Pulses", J. Physiol. (1977), 273, pp. 539-560, 22 pgs.
Papademetriou, et al., "Renal Sympathetic Denervation: Hibernation or Resurrection?", Cardiology 2016; 135, 11 pgs.
U.S. Appl. No. 17/453,636, filed Nov. 4, 2021.
"U.S. Appl. No. 15/996,978, Response filed Apr. 6, 2020 to Restriction Requirement dated Feb. 7, 2020", 8 pages.
"U.S. Appl. No. 15/996,978, Restriction Requirement dated Apr. 16, 2020", 8 pages.
"U.S. Appl. Serial No. 15/943,354, Non Final Office Action dated Apr. 20, 2020", 7 pages.

(56) References Cited

OTHER PUBLICATIONS

"U.S. Appl. No. 15/996,978, Response filed May 1, 2020 to Restriction Requirement dated Apr. 16, 2020", 8 pages.
"U. S. Appl. No. 15/996,978, Non Final Office Action dated Jun. 11, 2020", 8 pages.

* cited by examiner

INTRALUMINAL MICRONEUROGRAPHY DENERVATION PROBE WITH RADIO FREQUENCY ABLATION

CROSS-REFERENCE TO RELATED APPLICATIONS

This application is a continuation application of U.S. application Ser. No. 15/299,694 filed Oct. 21, 2016, which in turn is a continuation application of U.S. application Ser. No. 15/204,349, filed Jul. 7, 2016. The latter claimed the benefit of U.S. Provisional Application No. 62/198,382, filed Jul. 29, 2015. The benefit of priority of U.S. application Ser. Nos. 15/299,694, 15/204,349, and Provisional Application No. 62/198,382 are all claimed herein, and the contents of each are herein incorporated by reference.

FIELD

The invention relates generally to neural measurement, and more specifically to an intraluminal microneurography probe with radio frequency or microwave ablation.

BACKGROUND

The human body's nervous system includes both the somatic nervous system that provides sense of the environment (vision, skin sensation, etc.) and regulation of the skeletal muscles, and is largely under voluntary control, and the autonomic nervous system, which serves mainly to regulate the activity of the internal organs and adapt them to the body's current needs, and which is largely not under voluntary control. The autonomic nervous system involves both afferent or sensory nerve fibers that can mechanically and chemically sense the state of an organ, and efferent fibers that convey the central nervous system's response (sometimes called a reflex arc) to the sensed state information. In some cases, the somatic nervous system is also influenced, such as to cause vomiting or coughing in response to a sensed condition.

Regulation of the human body's organs can therefore be somewhat characterized and controlled by monitoring and affecting the nerve reflex arc that causes organ activity. For example, the renal nerves leading to the kidney can often cause a greater reflexive reaction than desired, contributing significantly to hypertension. Measurement of the nerve activity near the kidney, and subsequent ablation of some (but not all) of the nerve can therefore be used to control the nervous system's overstimulation of the kidney, improving operation of the kidney and the body as a whole.

Because proper operation of the nervous system is therefore an important part of proper organ function, it is desired to be able to monitor and change nervous system function in the human body to characterize and correct nervous system regulation of internal human organs.

SUMMARY

One example embodiment of the invention comprises an intraluminal microneurography probe, having a probe body that is substantially cylindrical and that is configured to be introduced into an artery near an organ of a body without preventing the flow of blood through the artery. An expandable sense electrode is fixed to the probe body at one end of the sense electrode and is movable relative to the probe body at a second end of the sense electrode such that movement of the movable end toward the fixed end causes the sense electrode to expand from the probe body toward a wall of the artery, and an expandable stimulation electrode is fixed to the probe body at one end of the stimulation electrode and movable relative to the probe body at a second end of the stimulation electrode such that movement of the movable end toward the fixed end causes the sense electrode to expand from the probe body toward a wall of the artery. A radio frequency ablation element is configured to ablate nerve tissue in the vicinity of the expandable sense and stimulation electrodes. A ground electrode is configured to couple to the body, and a plurality of electrical connections are operable to electrically couple at least the expandable sense electrode, expandable stimulation electrode, ground electrode, and radio frequency ablation element to electrical circuitry.

In further examples, the radio frequency ablation element comprises one or more monopole, dipole, loop, or ring antennas, or a phase-steered array of antennas. In further examples, the probe further comprises at least one of a cooling element configured to cool the probe in the vicinity of the radio frequency ablation element, and a reflector or shield configured to direct energy from the radio frequency ablation element in a specific direction.

In another example nerve activity associated with a body organ is characterized by introduction of a probe into artery to a location proximate to the body organ, and expansion of an expandable sense electrode and an expandable stimulation electrode comprising a part of the probe to contact the artery wall while permitting blood flow around the expanded sense and stimulation electrodes. An electricity source coupled to the stimulation electrode is used to excite the stimulation electrode, and the expanded sense electrode is used to measure sympathetic nerve activity as a result of exciting the stimulation electrode. A radio frequency ablation element is used to ablate nerves in the vicinity of the location proximate to the body organ such as via a radio frequency ablation element comprising a part of the probe, and re-excitation of the stimulation electrode using an electricity source coupled to the stimulation electrode, and re-measurement of sympathetic nerve activity as a result of exciting the stimulation electrode using the expanded sense electrode are performed to confirm the effects of the ablation The details of one or more examples of the invention are set forth in the accompanying drawings and the description below. Other features and advantages will be apparent from the description and drawings, and from the claims.

DETAILED DESCRIPTION

Figure 1:
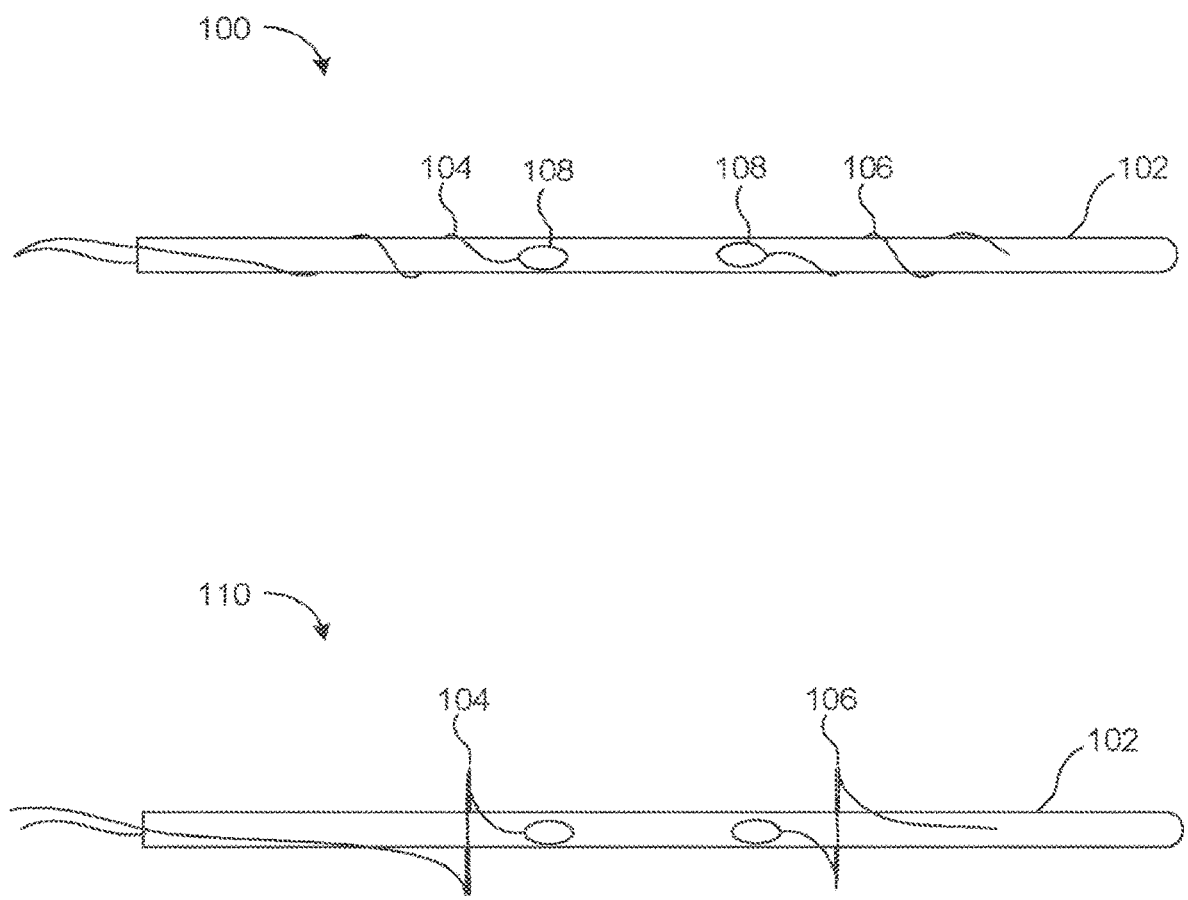
FIG. 1 illustrates an intraluminal microneurography probe having expandable helical wire electrodes, consistent with an example.

In the following detailed description of example embodiments, reference is made to specific example embodiments by way of drawings and illustrations. These examples are described in sufficient detail to enable those skilled in the art to practice what is described, and serve to illustrate how elements of these examples may be applied to various purposes or embodiments. Other embodiments exist, and logical, mechanical, electrical, and other changes may be made. Features or limitations of various embodiments described herein, however important to the example embodiments in which they are incorporated, do not limit other embodiments, and any reference to the elements, operation, and application of the examples serve only to define these example embodiments. Features or elements shown in various examples described herein can be combined in ways other than shown in the examples, and any such combination is explicitly contemplated to be within the scope of the examples presented here. The following detailed description does not, therefore, limit the scope of what is claimed.

Regulating operation of the nervous system to characterize and improve organ function includes in some examples introduction of a probe such as a needle, catheter, wire, or the like into the body to a specified anatomical location, and partially destroying or ablating nerves using the probe to destroy nerve tissue in the region near the probe. By reducing nerve function in the selected location, an abnormally functioning physiological process can often be regulated back into a normal range.

Unfortunately, it is typically very difficult to estimate the degree to which nerve activity has been reduced, which makes it difficult to perform a procedure where it is desired to ablate some, but not all, nerves to bring the nervous system response back into a desired range without destroying the nervous system response entirely.

One such example is renal nerve ablation to relieve hypertension. Various studies have confirmed that improper renal sympathetic nerve function has been associated with hypertension, and that ablation of the nerve can improve renal function and reduce hypertension. In a typical procedure, a catheter is introduced into a hypertensive patient's arterial vascular system and advanced into the renal artery. Renal nerves located in the arterial wall and in regions adjacent to the artery are ablated by destructive means such as radio frequency waves, ultrasound, laser or chemical agents to limit the renal sympathetic nerve activity, thereby reducing hypertension in the patient.

Unfortunately, renal nerve ablation procedures are often ineffective, such as due to either insufficiently ablating the nerve or destroying more nerve tissue than is desired. Clinicians often estimate based on provided guideline estimates or past experience the degree to which application of a particular ablative method will reduce nerve activity, and it can take a significant period of recovery time (3-12 months) before the effects of the ablation procedure are fully known.

Some attempt has been made to monitor nerve activity in such procedures by inserting very small electrodes into or adjacent to the nerve body, which are then used to electrically monitor the nerve activity. Such microneurography practices are not practical in the case of renal ablation because the renal artery and nerves are located within the abdomen and cannot be readily accessed, making monitoring and characterization of nerve activity in a renal nerve ablation procedure a challenge.

Prior methods such as inserting electrodes into the arteries of a patient's heart and analyzing received electrical signals are not readily adaptable to renal procedures, as arteries in the heart are generally large and more readily accommodate probes for performing such measurements. Further, the cardiac electrical signals emitted from the heart are generally large and slow-moving relative to electrical signals near the renal arteries, which tend to be smaller in size and produce smaller signals that propagate more quickly through the nerves. As such, intravascular techniques used in heart measurements are readily adaptable to similar renal processes.

Because nerve activity during organ procedures such as renal nerve ablation cannot be readily measured, it is also difficult to ensure that an ablation probe is located at the most appropriate sites along the renal artery, or to measure the efficiency of the nerve ablation process in a particular patient.

Some examples presented herein therefore provide an improved probe and method for characterizing nerve activity near an organ such as a kidney, including electrodes configured specifically to measure nerve activity in an environment different from the heart while permitting blood flow around the probe. In a more detailed example, the probe includes a sense electrode and a stimulation electrode that are expandable from a body of the probe, which can be introduced via a sheath. The sheath in a further embodiment comprises one or more electrodes, such as one or more sense electrode reference or ground electrodes.

FIG. 1 illustrates an example of such a probe. Here, a probe assembly is shown generally at 100, including probe body 102, and first and second helical electrodes 104 and 106. Each of the helical electrodes is attached to the probe body at one end, shown here as an attachment point 108, such as an epoxy bead or other suitable attachment mechanism. The opposite end of each of the helical electrodes is constrained in the example shown, such as by emerging through a hole in the probe as shown by helical electrode 106, and extends from the left end of the probe assembly to connect to electronic instrumentation to perform various functions. The configuration of the helical electrode wires is such that the wires will expand about the axis of the probe body 102 when the wire of each helical electrode is forced toward the attachment points 108, causing the wire to form a circular shape having a diameter substantially larger than the helical electrode wires in the collapsed position, as shown at 100.

The probe assembly is shown again at 110, here with the helical electrode wires 104 and 106 forced toward the attachment points 108, causing the wire to expand away from the probe body 102. This helical expansion allows the helical electrodes to expand in an environment such as an artery such as to contact the artery walls while allowing blood to flow around the probe body 102 and past the helical electrodes 104 and 106.

Figure 2:
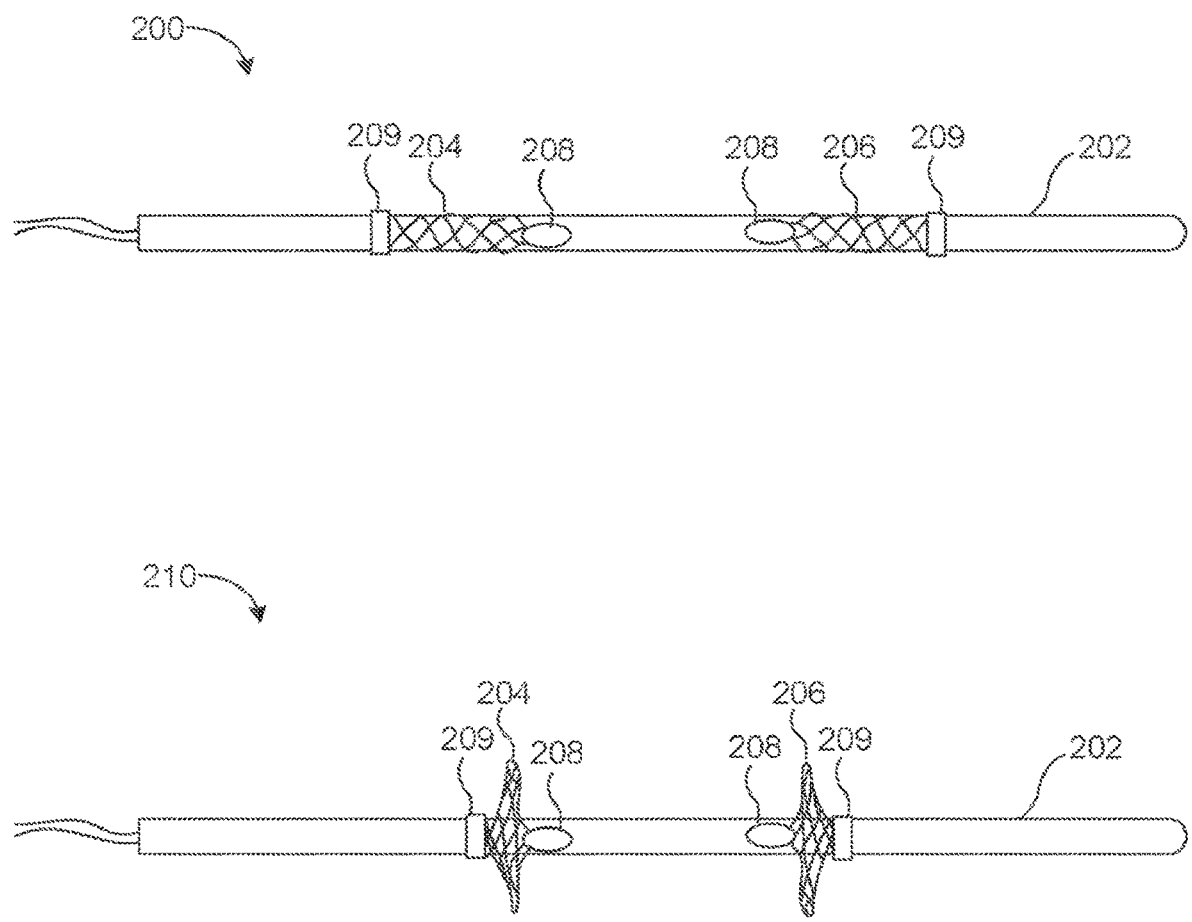
FIG. 2 illustrates an intraluminal microneurography probe having expandable wire mesh electrodes, consistent with an example.

Another example of a probe configured to characterize nerve activity near an organ such as a kidney while permitting blood flow around the probe is shown in FIG. 2. Here, a probe body is shown at 202, having mesh electrodes 204 and 206 affixed thereto at attachment points 208. The mesh electrodes are substantially similar to the helical wire electrodes of FIG. 1, except that several such electrodes are interwoven to form a mesh that is closely wrapped around the probe body 202. In this example, each mesh electrode also has a sliding collar element 209 located at the end of the mesh electrode opposite attachment point 208.

This sliding collar 209 when moved toward the attachment point 208 causes the mesh to expand around the probe body 202, as shown generally at 210. Here, the expanded mesh electrodes 204 and 206 are configured to provide electrical contact, such as with an artery wall, in a diameter significantly larger than the diameter of the probe body 202. This enables insertion of the probe body into an artery, and expansion of the electrodes 204 and 206 to contact the artery walls, without blocking blood flow through the artery. Although the examples of FIGS. 1 and 2 show two probe configurations that can achieve such functions, probe configurations other than those shown here may also be configured to achieve these or similar functions.

Figure 3:
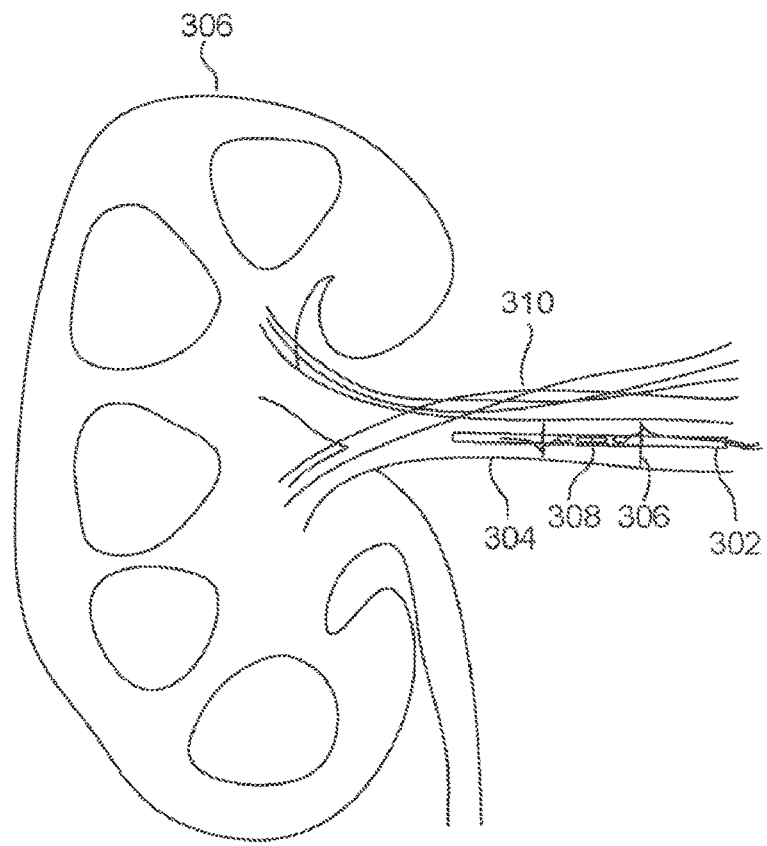
FIG. 3 shows introduction of an intraluminal microneurography probe into an artery in a location near a kidney, consistent with an example.

FIG. 3 illustrates one example of use of such a probe, in which a probe 302 such as that shown in FIG. 1 or FIG. 2 is introduced into a blood vessel, such as an artery 304, in a location near a body organ such as kidney 306. The probe is introduced via a sheath in some examples, such as where a sheath is advanced to the intended probe location in the artery, and then withdrawn sufficiently to expose the probe 302 to the artery 304. The probe 302 here comprises a stimulation electrode such as electrodes 104 and 204 of FIGS. 1 and 2, and a sense electrode such as electrodes 106 and 206 of the same Figures.

When deployed, the electrodes are expanded as shown at 308, such that they are near or touch the walls of the artery 304. The electrodes are thereby located nearer the nerve bundle 310 connecting the kidney to the central nervous system, as the nerve bundle tends to approximately follow the artery leading to most body organs. As shown at 310, the nerve bundle tends to follow the artery more closely at the end of the artery closer to the kidney, while spreading somewhat as the artery expands away from the kidney. As a result, it is desired in some examples that the probe is small enough to introduce relatively near the kidney or other organ, as nerve proximity to the artery is likely to be higher nearer the organ.

When in place, a practitioner can use instrumentation coupled to the sense electrode and stimulation electrode to stimulate the nerve, and monitor for nerve response signals used to characterize the nervous system response to certain stimulus. In a further example, an ablation element 308 is configured to ablate nerve tissue, such as by using radio frequency, ultrasound, or other energy, such that the probe can actively stimulate the nerve and sense resulting neural signals in between applications of energy via the ablation element 308, enabling more accurate control of the degree and effects of nerve ablation. In other examples, a probe 302 lacking an ablation element can be remove via the sheath, and an ablation probe inserted, with the ablation probe removed and the probe 302 reinserted to verify and characterize the effects of the ablation probe.

Figure 4:
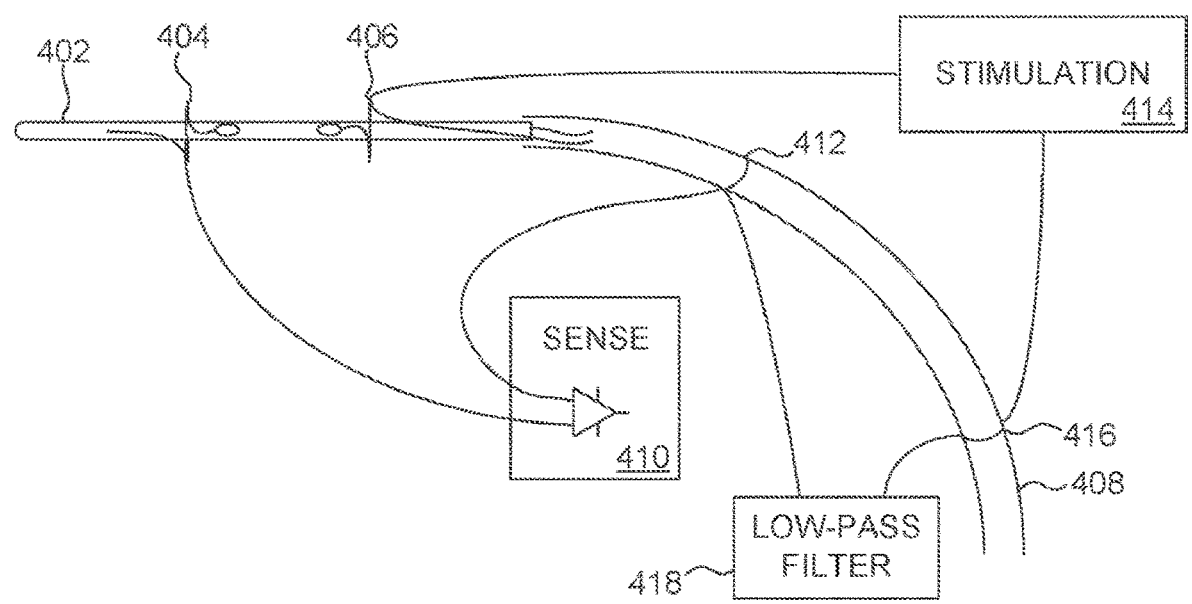
FIG. 4 shows an intraluminal microneurography probe and sheath assembly coupled to associated instrumentation, consistent with an example.

FIG. 4 shows an intraluminal microneurography probe and sheath assembly coupled to associated instrumentation, consistent with an example. Here, a probe body 402 has an expandable sense electrode 404 and an expandable stimulation electrode 406, couple via wires to instrumentation. A sheath 408 is used to introduce the probe into an artery or other biological lumen or suitable location, and to carry instrumentation wires and mechanical connections used to manipulate the expandable electrodes. The electrodes are not shown here running through the sheath, but are instead shown as schematic links between the electrodes and various instrumentation circuitry for clarity.

In this example, the expandable sense electrode 404 is coupled to a sense circuit, such as a differential amplifier as shown at 410, with the other input to the sense amplifier circuit coupled to a ground electrode such as local ground electrode 412 coupled to the sheath 408. In another example, local ground electrode is located elsewhere, such as on the probe body 404. The expandable stimulation electrode 406 is similarly coupled to a stimulation circuit 414 that is operable to provide a stimulation voltage or current signal of a desired pulse shape, intensity, and duration to the expandable stimulation electrode 406, with reference to body ground. Body ground is established in this example by a body ground electrode 416, which is here also shown as coupled to the sheath 408, but which in other embodiments will take other forms such as an electrode coupled to the body's skin. Here, the body ground electrode 416 is further coupled to the local ground electrode 412 by use of a low-pass filter, having a frequency response or time constant selected such that the local ground electrode does not drift significantly from the body ground level but retains the ability to accurately detect and characterize local nerve impulses.

The electrodes in this example comprise electrical wires that are significantly smaller than are used in other applications such as cardiac probes, in part because the pulse duration in the nerve bundle leading to most body organs is typically much shorter than a cardiac muscle excitation signal. In one embodiment, the sense electrode 404 therefore comprises a wire or mesh of wires having a diameter of 8-10 thousandths of an inch, while in other examples the wire diameter is 5-10 thousandths, 5-15 thousandths, or any size under 15, 10, 8, or 5 thousandths of an inch. The sense electrode is thereby configured to accurately detect a typical nerve action potential of 2 milliseconds traveling at a meter per second without smearing or distorting the measured pulse due to an overly large electrode.

The stimulation electrode in various examples comprises a wire or mesh of wires having any of the above sizes, but in another example, it is desired that the stimulation electrode 406 be substantially larger than the sense electrode 404 to avoid hyperpolarization of the nerve in the region of the electrode during stimulation.

Wire size of electrodes such as the sense electrode 404 is selected in further examples based on a typical nerve conduction velocity range of 0.4-2 meters/second, with nerve impulses ranging from 1-3 milliseconds. Also, the sense electrode 404 and stimulation electrode 406 are desirably placed a sufficient distance apart, such as 3 centimeters, to accurately detect a typical nerve action potential of 2 milliseconds without interference from the stimulation electrode.

Because the size of organ arteries such as the renal artery are typically in the range of 5 millimeters in diameter, it is desired to have a probe body that is a fraction of this size, such as having a diameter of 2.5 mm, 2 mm, 1 mm, or similar. This enables introduction of the probe without interfering with blood flow through the artery, such that the expandable electrodes can still expand to the artery walls without further significantly impeding blood flow.

Figure 5:
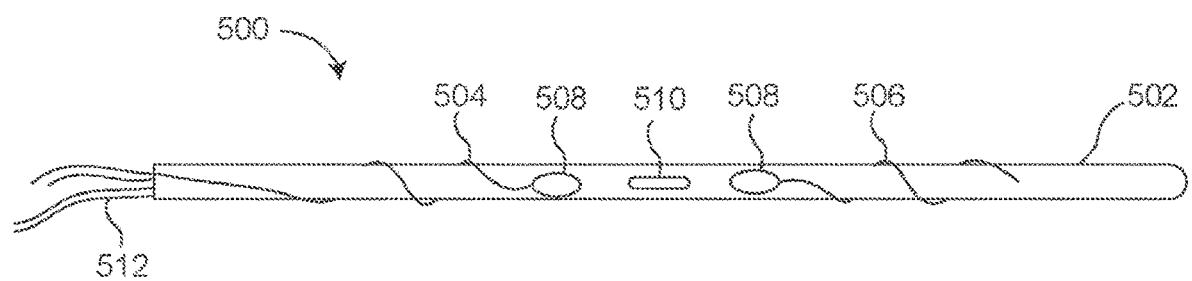
FIG. 5 shows an intraluminal microneurographic probe having an RF ablation antenna, consistent with an example.

FIG. 5 shows an intraluminal microneurographic probe having an RE ablation antenna, consistent with an example. The probe 500 in this example has a probe body 502 and first and second helical electrodes 504 and 506 as in the previous examples, and each of the helical electrodes is again attached to the probe body at one end as shown at 508. A Radio Frequency (RF) ablation antenna, such as a microwave antenna, is shown at 510, such as is shown at 308 in FIG. 3. The RF ablation antenna 510 is connected to a signal source using coaxial cable 512, such that the probe can actively stimulate the nerve and sense resulting neural signals using helical electrodes 504 and 506 in between applications of energy via the ablation element RF ablation antenna 510, providing more accurate control of the degree and effects of nerve ablation. The RF ablation antenna in various examples comprises a coil, a monopole or dipole, a reflector, a slot, a feedhorn, one or more rings, or combination of such elements to control ablation direction and heating in the region of the antenna. In a further example, a cooling element such as a liquid jacket or tube is provided to cool tissue not targeted by the RF ablation antenna, and in some examples to shield RE energy from such tissue.

Figure 6:
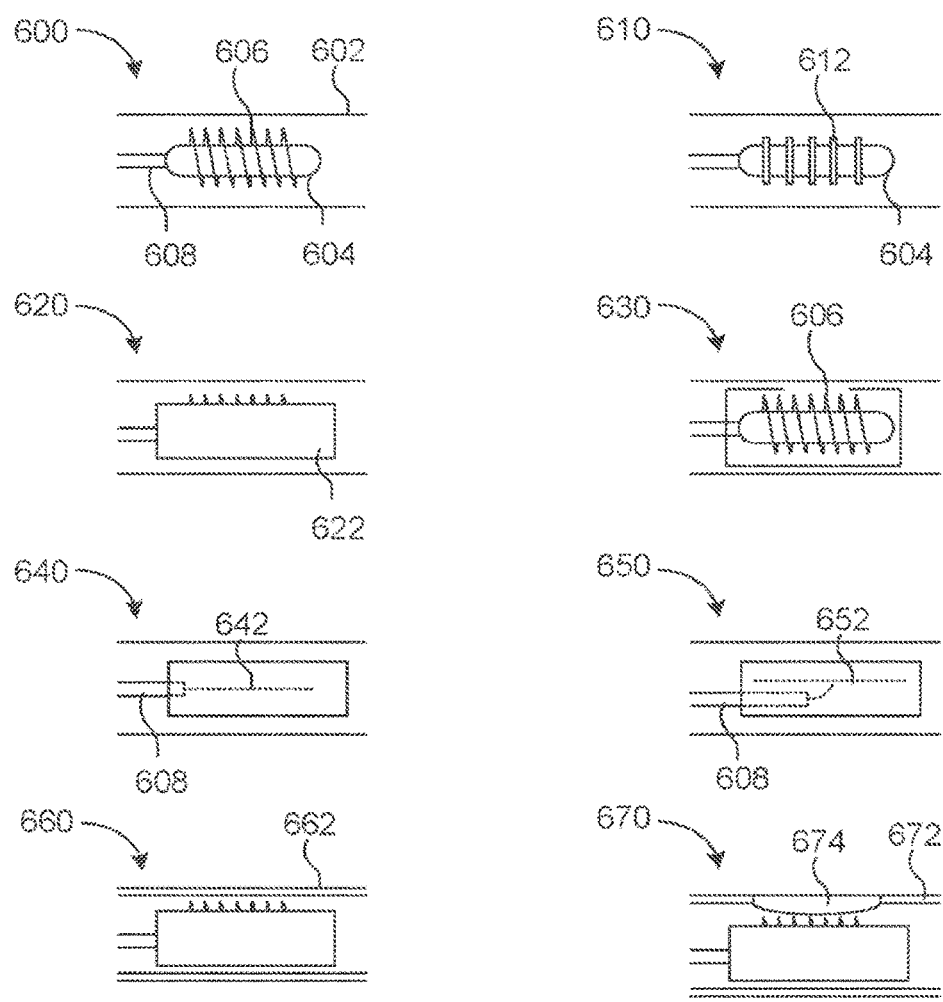
FIG. 6 shows a variety of RF ablation antenna configurations for an intraluminal microneurographic probe, consistent with various examples.

FIG. 6 shows RE ablation antenna configurations for an intraluminal microneurographic probe, consistent with various examples. In the example shown at 600, a probe body 602 includes an RF microwave ablation element having a core 604, and a coil element 606 coupled to a coaxial cable 608. In this example, the coil 606 serves as the microwave antenna, and in various examples it is wound around a ferrite or other ferromagnetic core, oriented differently than as shown, or shielded to restrict the direction of RF emission.

Another example microwave antenna configuration is shown at 610, in which a core 604 includes two or more rings or windings 612 that are spaced at least a fraction of a wavelength apart from one another. The phase of the signal provided to the two or more windings 612 can therefore be varied to control the radiation pattern of the microwave antenna, directing energy to adjacent tissue as desired. In a more detailed example, the phase, frequency, or other parameters of the energy supplied to the windings is controlled such as in a phase-steered array to target tissue at a certain depth or distance from the microwave probe for ablation.

Because the radiation pattern of the microwave antennas shown at 600 and 610 is approximately the same around the circumference of probe body 602, the example microwave antenna shown at 620 further comprises a reflector 622. Here, the reflector 622 wraps around the sides and bottom of the side view of the coil antenna as shown at 600, absorbing or reflecting radiation that is not directed upward as shown. This enhances the microwave antenna's capacity to target specific tissue, such as nerves, that are present in a known direction from the probe body 602.

In a similar example, the microwave antenna configuration shown at 630 includes a coil antenna 606 such as was shown at 600, but also includes a shield 632 around the antenna having an aperture 634 on the side of the shield configured to let radiation pass. The size, position, and other configuration parameters of the aperture 634 are therefore configured to pass radiation in the direction of nerve tissue to be ablated, while shielding radiation from being emitted in other directions unnecessarily. Combining technologies such as shielding and phase steering can be used in a further example to control both the direction and depth of emitted radiation, targeting tissue with greater discrimination than a simple coil antenna such as that shown at 600.

The microwave antenna in other examples comprises a configuration other than a coil or coils, such as a monopole or dipole antenna. A monopole microwave antenna is shown in the example at 640, where a coaxial cable 608 is coupled to an antenna element 642. Here, the coaxial cable is connected to one end of the antenna element 642, and the coaxial cable provides microwave energy to the antenna to ablate nearby nerve tissue. The frequency of the microwave energy and the antenna are typically configured so that the antenna is a quarter wavelength or longer relative to the microwave energy being provided.

At 650, a dipole antenna 652 is similarly configured, coupled to the coaxial cable and to a microwave power source in the center of the antenna 652 rather than at one end. This configuration makes the antenna 652 a dipole antenna rather than a monopole as shown at 640/642. Although the radiation pattern from a monopole antenna is primarily perpendicular to the antenna, it can vary in width and have lobes at varying angles from perpendicular depending on the wavelength of the microwave energy signal provided and the length of the antenna. The dipole antenna shown at 650/652 can be configured to have, a single, narrow lobe of radiated energy perpendicular to the antenna, which may be of greater value in targeting tissue for ablation. In a further example, multiple monopole or dipole antenna elements are provided, such as shown at 610, and phase steering or other such methods are used to enhance control over the direction and depth of radiated microwave power.

Because the nerve or other tissue being ablated is typically on only one side of the probe body 602, shields or apertures such as those shown at 620 and 630 may be employed with various microwave antenna configurations to limit emission of RF energy to the direction of the tissue to be ablated. Because microwave antennas can cause significant heating in tissue surrounding the antenna, some probe examples also include one or more cooling elements, such as a coolant jacket, in the vicinity of the microwave antenna. At 660, an antenna with a shield such as is shown at 620 is provided, along with a probe body having both an inner and outer wall forming a cooling jacket 662. The cooling jacket in this example reduces heating from the antenna in the region immediately surrounding the probe body, such as from a heated antenna coil or other element, or from a reflector or shield. In a more detailed example, cooling fluid is circulated within the cooling jacket, such as by a cooling fluid pump feeding coolant to the probe assembly.

In another example shown at 670, a probe assembly has a cooling jacket 672 that does not extend around the entire probe body in the vicinity of the microwave antenna. In a more detailed example, the cooling jacket 672 is interrupted by probe body portion through which coolant does not flow, such as the cooling jacket aperture shown at 674. In a further example, the cooling jacket comprises a metallic material that can also shield microwave energy from traversing through the cooling jacket, while the cooling jacket aperture 674 comprises a material that not metallic and that allows microwave energy to be emitted through that portion of the probe body. Such a configuration provides for selective microwave radiation in the desire direction, and also places cooling fluid or other cooling elements in close contact with metallic shield portions of the probe to more effectively cool the metallic shield elements.

An intraluminal microneurography probe such as those shown in FIGS. 1-6 can be introduced into an artery via a sheath, and used to monitor nerve activity during normal operation of an organ. This enables characterization of nerve activity in the organ, such as to diagnose or treat a variety of conditions. In one such example, a probe is used for characterization of overactive nerves reaching the kidney in patients suffering from hypertension, and to monitor ablation of the nerves to a point where nerve activity is in the desired range as measured using the probe. In other examples, the probe may be used while other actions are performed, such as to monitor nerve activity to a patient's prostate while surgery or other methods remove material to treat prostate cancer or enlarged prostate problems. Because it is desirable that significant nerve connection to the prostate be preserved during such procedures, a probe such as those presented here can be used to minimize the chances of nerve damage that may affect normal function of the prostate.

A probe such as those shown here can also be used to diagnose various organ dysfunctions, such as where an organ overreacts to nerve impulses or overstimulates the nerve in response to organ activity. The probe is here described in some examples as an intraluminal probe, meaning the probe may be introduced into various lumina or pathways in the body, such as arteries, veins, the gastrointestinal tract, pathways of bronchii in the lungs, pathways of the genitourinary tract, and other such pathways. The probe is neurographic in the sense that it enables characterization, such as measurement, recording, and visualization of neurologic activity in the vicinity of the probe. Because the autonomic nervous system regulates a wide variety of functions within the body, including circulation, digestion, metabolism, respiration, reproduction, etc. by a network of parasympathetic and sympathetic nerves that typically accompany the blood vessels supplying blood to the organs they regulate, an intraluminal neurographic probe such as those described here can be used to measure or characterize the regulation of many of these functions by introducing the probe into the blood vessels near the organ of interest.

Although the example of FIG. 3 illustrates ablation of nerves near the kidney to regulate kidney function in treating hypertension, nerves regulating liver function accompany the hepatic artery and the portal vein, nerves regulating the stomach accompany the gastroduodenal arteries, nerves from the superior mesenteric plexus accompany the superior mesenteric artery and branch to the pancreas, small intestine and large intestine, and nerves of the inferior mesenteric plexus accompany the inferior mesenteric artery and branch to the large intestine, colon and rectum. These examples illustrate other organs that can be characterized and regulated using probes and techniques such as those described herein.

In treating kidney function, it is significant that renal sympathetic nerves have been identified as a major contributor to the complex pathophysiology of hypertension. Patients with hypertension generally have increased sympathetic drive to the kidneys, as evidenced by elevated rates of the renal norepinephrine "spillover." It is therefore believed that ablating renal sympathetic nerve function with sufficient energy will cause a reduction in both systolic and diastolic blood pressure, relieving hypertension in the patient.

Studies have shown that most nerves surrounding the renal arteries are within two millimeters of the renal artery, with nerves clustered more closely around the artery near the kidney, making measurement and treatment of the nerves from the renal artery practical. But, as complete destruction or ablation of the nerves is likely not desirable, monitoring nerve activity during or between nerve ablations, such as via the probes described herein, is an important tool in characterizing and regulating the degree to which nerve activity has been reduced. Before introduction of probes such as those described here, clinicians were unable to readily determine extent of renal sympathetic nerve modification during a procedure in a clinically relevant timeframe, and could not measure durability of nerve damage during follow-up period after denervation. Now, with probes such as those described herein available, a clinician can take such measurements, and can to asses health of renal sympathetic nerves pre-procedurally to select or screen patients for denervation.

In operation, a clinician can measure nerve activity such as renal sympathetic nerve activity (RSNA) by emitting an electrical pulse through stimulation electrodes in the probe, and recording propagation along renal sympathetic nerve fibers using the sense electrode or electrodes on the probe. The clinician can then compare RSNA pre- and post-denervation to determine the degree of nerve ablation incurred, thereby more accurately achieving the desired degree of nerve ablation during treatment of the patient. More specifically, a clinician can apply an electrical stimulus to a site in the proximal renal artery, and then monitor or record the nerve activity between the stimulus site and the kidney, thereby measuring the resultant downstream action potential in the nerve. Nerve ablation is then performed, and the stimulus and measurement of the nerve is repeated to verify a reduced or eliminated evoked potential detected in the nerve as a result of stimulation via the probe's electrodes.

The probe examples described in the examples here can therefore provide real-time feedback on functionality of renal sympathetic nerves, providing integrated evaluation of all nerve fibers surrounding a renal artery, at the artery proximal, distal, and renal branch locations. The probe is easily deployed via catheter-based delivery, and can be used as a standalone product or integrated with an ablation element. The probe system's low hardware and software costs and easy learning curve for clinical users make the probe system well-adapted for widespread adoption for treatment of nerve conditions such as those described herein.

A variety of experiments have been conducted to verify operation of probes such as those described herein, including using an isolated canine/porcine kidney and the associated vasculature to conduct certain tests. In one such test, probes such as those of FIGS. 1-6 were used to verify renal nerve health by measuring spontaneous renal sympathetic nerve activity (RSNA) using intraluminal microneurography, demonstrating that such probes cause effective stimulation and recording of RSNA. In the tests, stimulus-elicited response established a baseline recording of RSNA, and the circumferential section of renal nerve fibers were damaged using a scalpel. Re-measuring the stimulus-elicited response and comparing the response to the established baseline recording of RSNA confirmed that spontaneous sympathetic renal nerve activity had been reduced.

Figure 7:
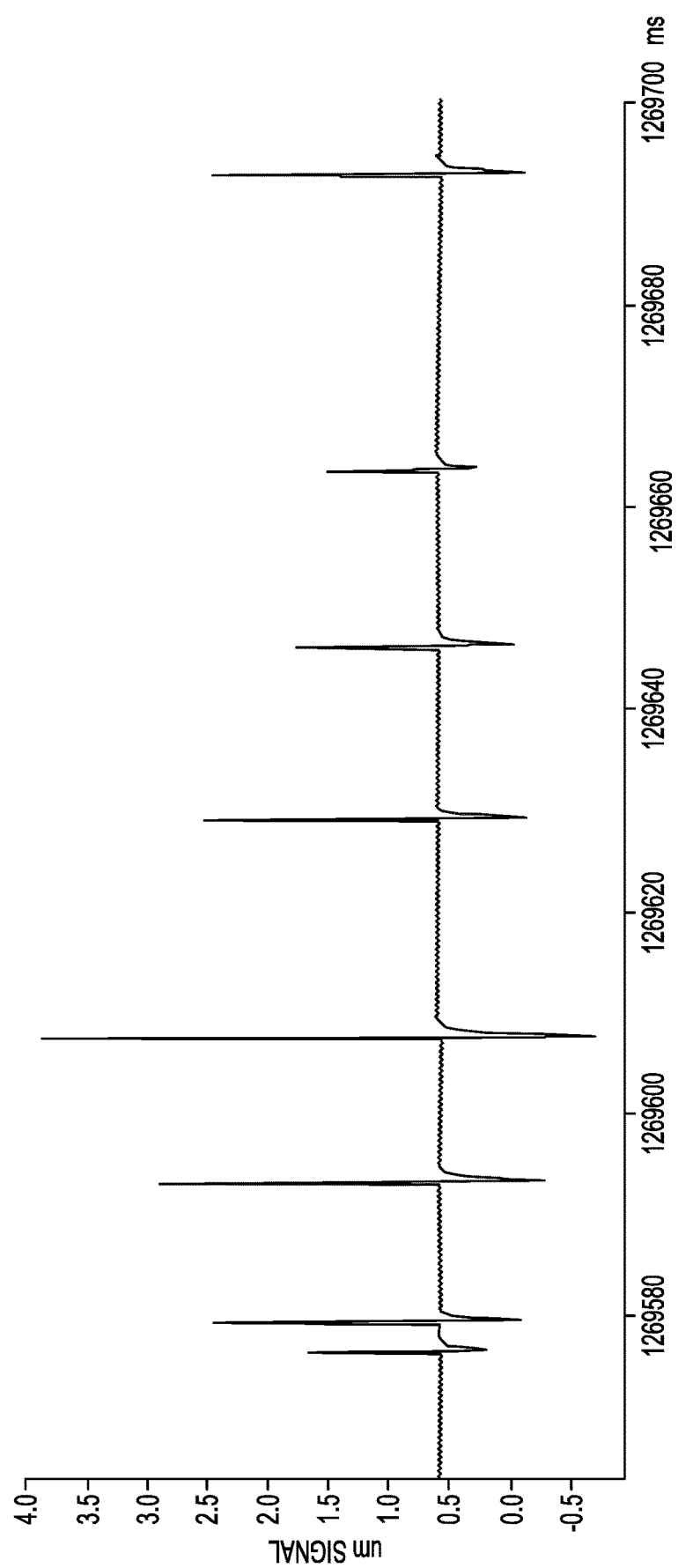
FIG. 7 shows spontaneous nerve activity, measured from the wall of the renal artery of an explanted kidney, consistent with an example.

FIG. 7 shows spontaneous nerve activity measured from the wall of the renal artery of an explanted kidney. Here, the measurements are taken using needles placed in the wall of the renal artery, using relatively invasive microneurography techniques.

Figure 8:
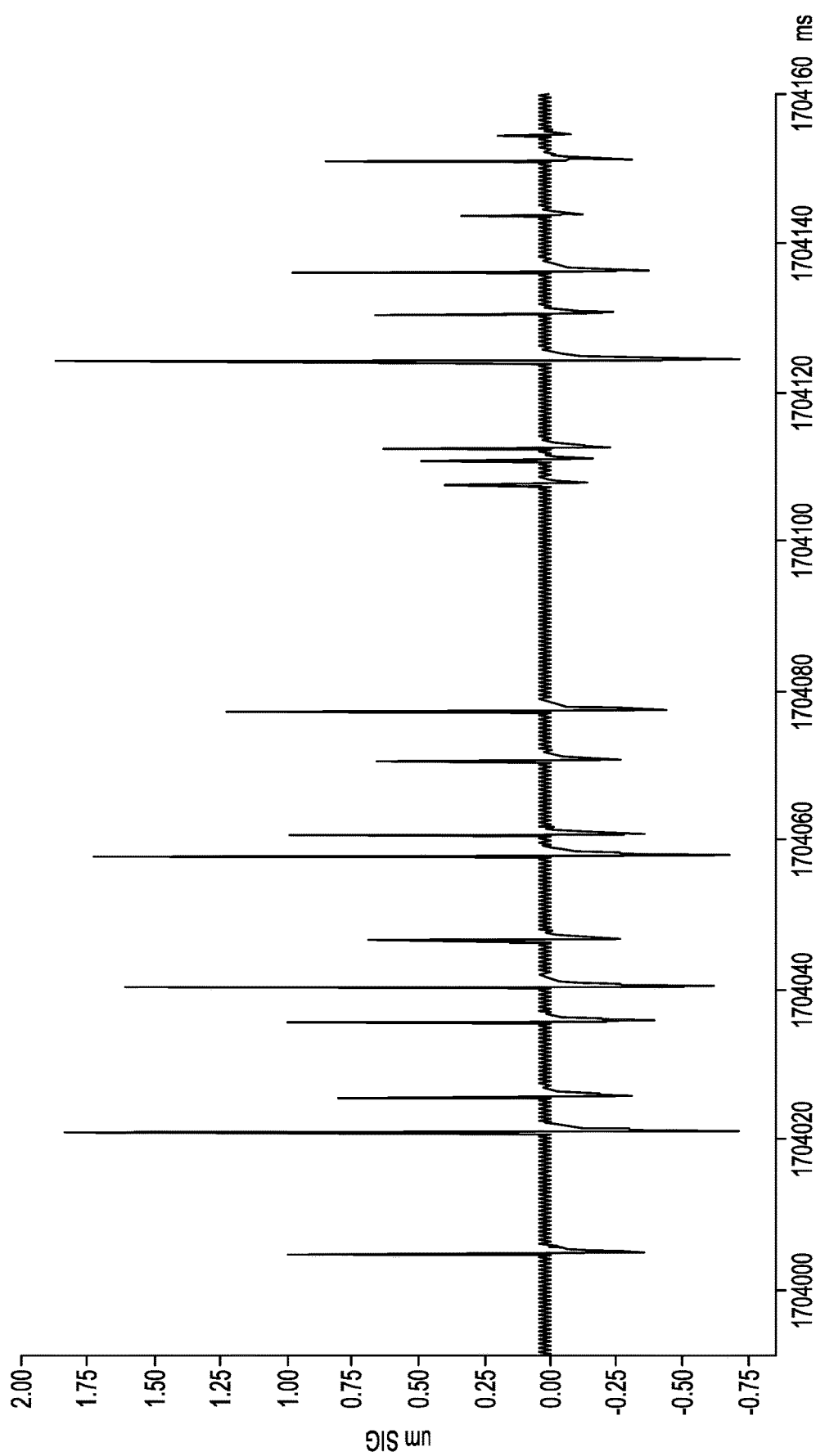
FIG. 8 shows spontaneous nerve activity in the wall of the renal artery of an explanted kidney using an intraluminal microneurography probe, consistent with an example.

FIG. 8 shows spontaneous nerve activity in the wall of the renal artery of an explanted kidney, using an intraluminal microneurography probe. Here, the peak signal levels are somewhat reduced relative to the method of FIG. 5, but accurate detection, measurement, and recording of spontaneous RSNA signals is shown to be achieved.

Figure 9:
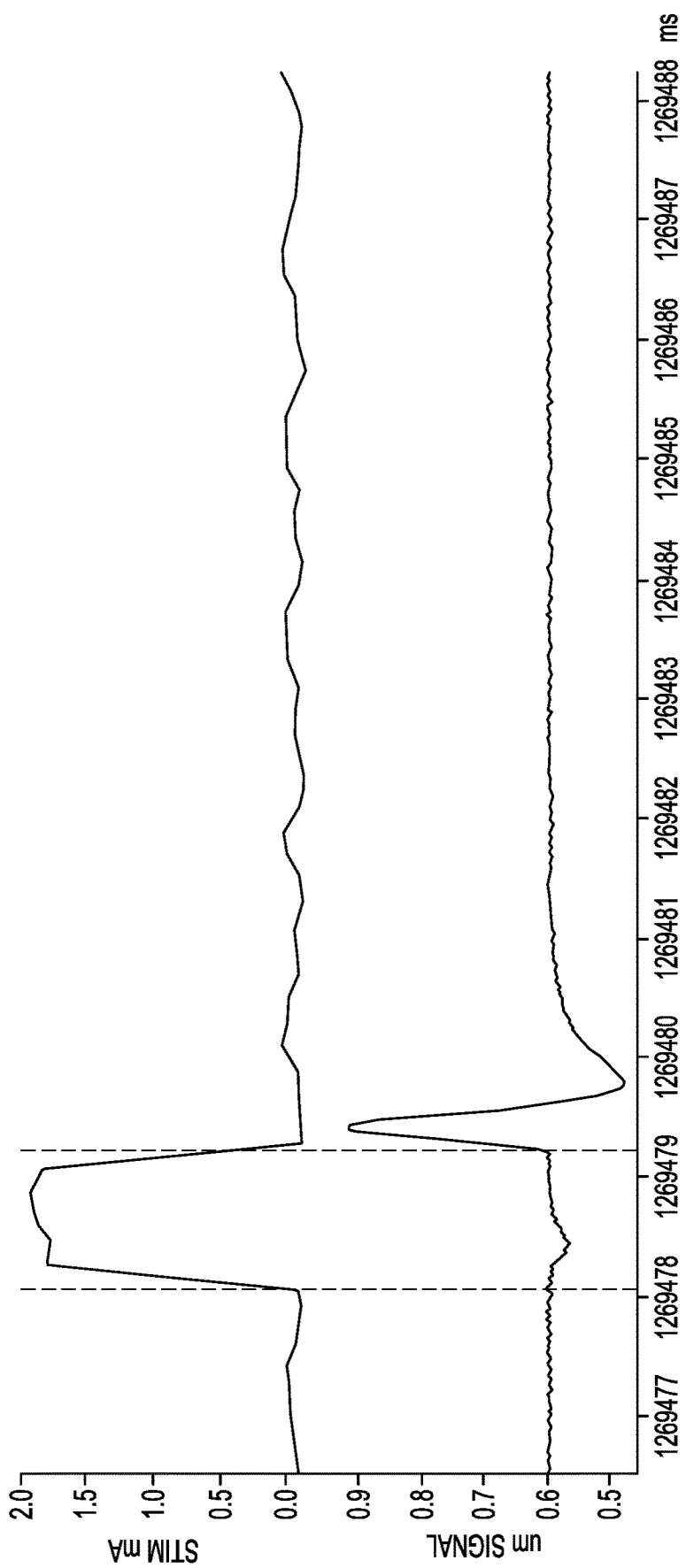
FIG. 9 shows a stimulus signal and the resulting measured RSNA action potential, consistent with an example.

In FIG. 9, a stimulus signal (top) and the resulting measured RSNA action potential are shown. Here, the renal nerve RSNA action potential is measured using needles in the artery wall, using a stimulus time of approximately 1.3 milliseconds, configured to avoid overlapping the stimulus and response signals based on the expected conduction velocity and the selected stimulus and sense electrode spacing.

Subsequent testing on live animals also proved successful, with a series of experiments conducted in a live rat model to confirm detection of renal sympathetic nerve activity (RSNA) in a living animal with competing signals from cardiac electrical activity and respiratory movement. Excellent results were achieve using probes having configurations such as those described herein, based on an experimental procedure in which an evoked RSNA baseline was determined in the intact renal artery, and RSNA was measured as the renal artery was transected.

Figure 10:
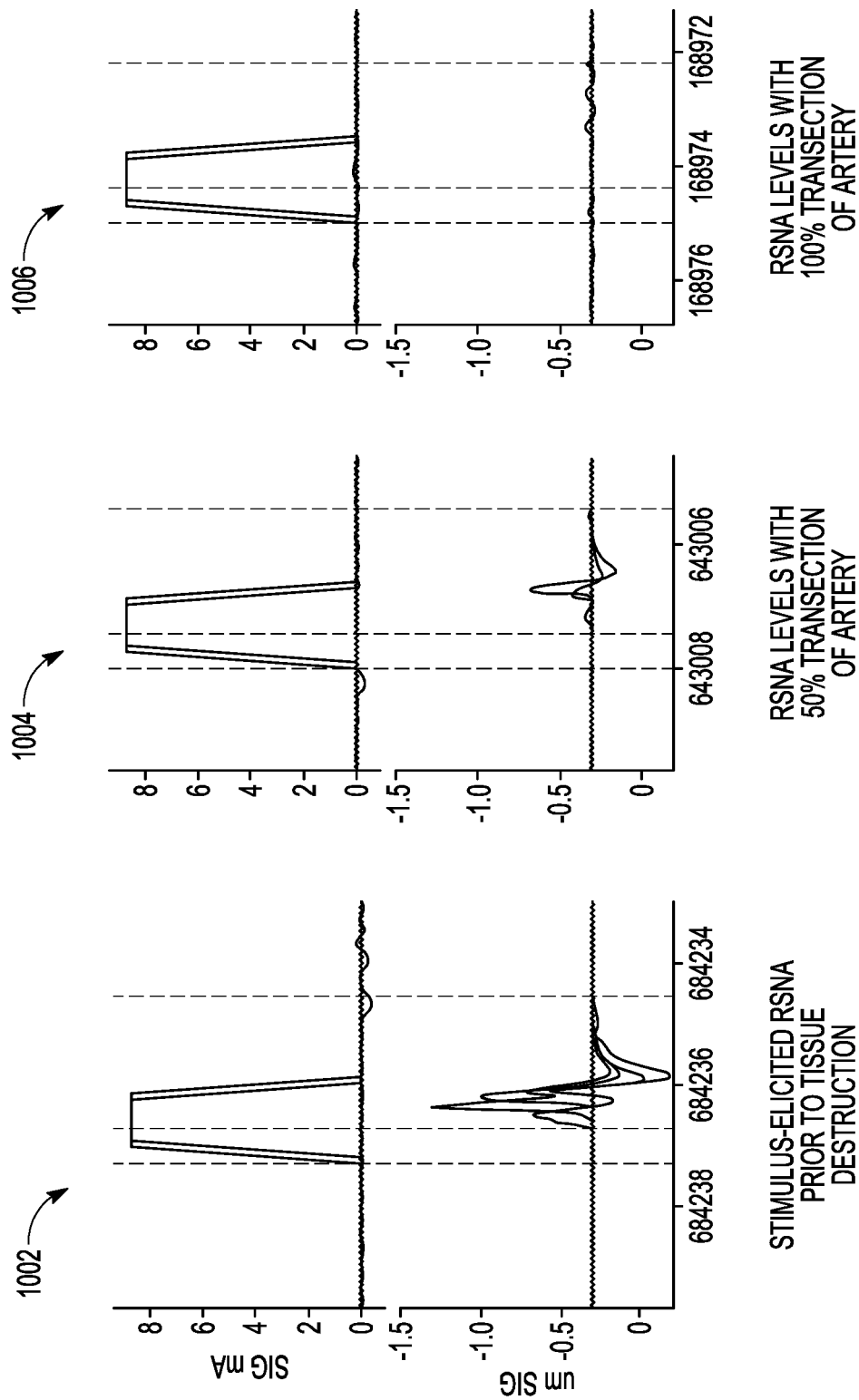
FIG. 10 shows destruction of the renal sympathetic nerves and the resulting effects on RSNA signals measured as a result of an applied stimulus signal, consistent with an example.

Destruction of the renal sympathetic nerves, and the resulting effects on RSNA signals measured as a result of an applied stimulus signal, are shown in FIG. 10. Here, ten sets of data are overlaid to generate a graph representative of typical levels and distribution of RSNA response to a stimulus signal as varying degrees of arterial transection. At 1002, the evoked RSNA baseline measurements taken prior to cutting across the artery are taken as a reference. At 1004, the artery is 50% transected, resulting in significant reduction in observed RSNA response, and at 1006, the artery is 100% transected, and little to no RSNA response is observed. In this example, transection of the renal arteries was used to destroy renal neural pathways because rat renal arteries are too small for effective radio frequency ablation.

Figure 11:
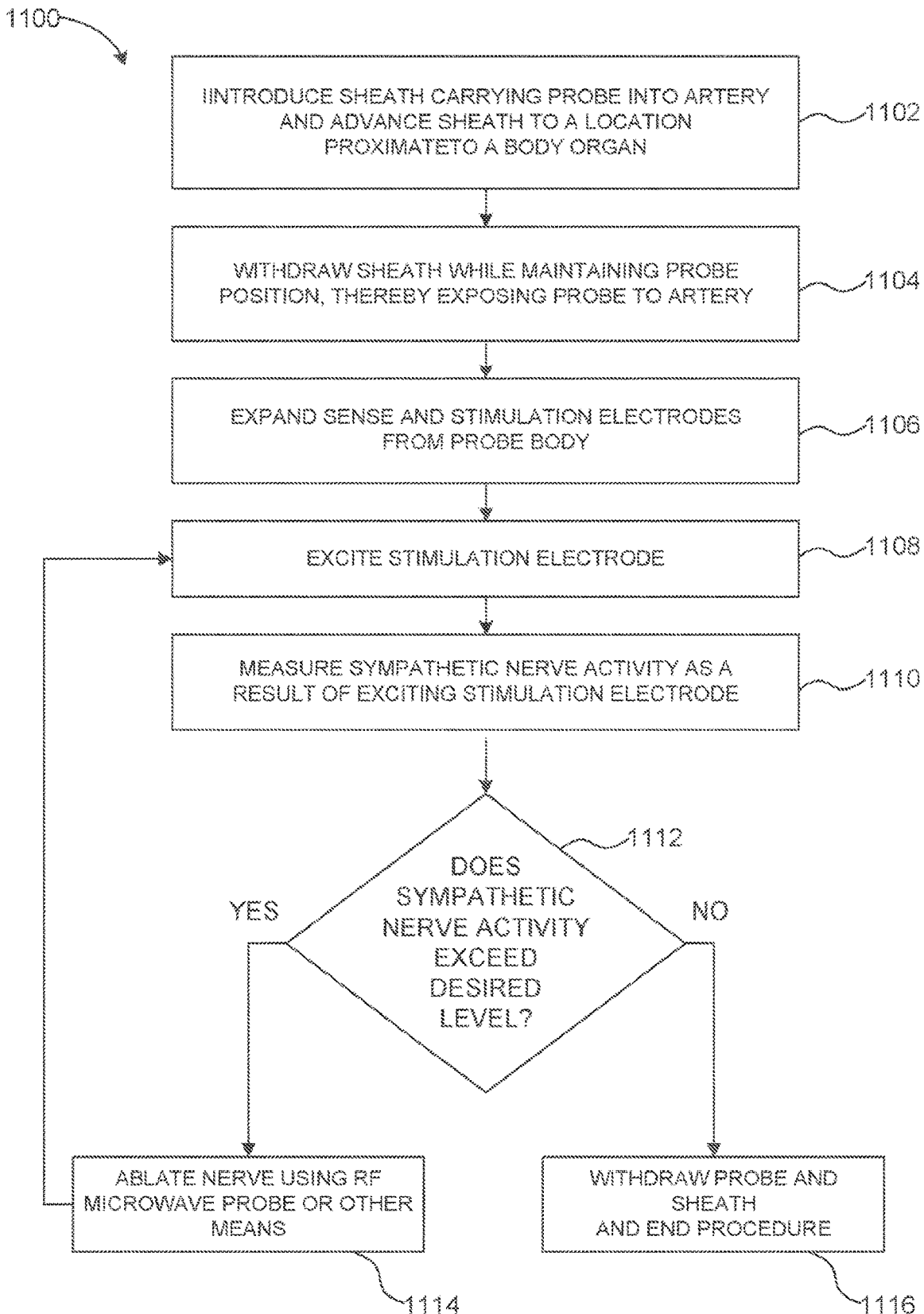
FIG. 11 is a flowchart illustrating a method of using an intraluminal microneurography probe to treat a medical condition, consistent with an example.

FIG. 11 is a flowchart illustrating a method of using an intraluminal microneurography probe to treat a medical condition, consistent with an example. As shown generally at 1100, a method of treating a medical condition involves using probe to excite and measure nerve activity near an organ, and selectively ablating nerve tissue near the probe until the desired nerve activity in response to the excitation is observed.

A sheath carrying the probe into the artery is inserted at 1102, and is advanced to a location in the artery near a body organ that is the subject of the medical condition and treatment, such as treating a kidney's neural sympathetic response to treat hypertension. The sheath is withdrawn slightly at 1104, exposing at least part of the probe including an expandable sense electrode and an expandable stimulation electrode to the artery. At 1106, the expandable stimulation and sense electrodes are expanded, such that the electrodes contact the arterial wall while permitting blood flow around the probe and the electrodes. At this point, the probe is properly deployed and ready to perform measurement.

The expandable stimulation electrode is excited at 1108, inducing an electrical signal into the nerves adjacent to the arterial wall. The nerves propagate the signal from the stimulation electrode, which can be observed at 1110 as sympathetic nerve activity as a result of exciting the stimulation electrode. The observed sympathetic nerve activity can then be measured, characterized, stored, viewed, etc., to determine whether the sympathetic nerve activity exceeds a desired level at 1112. If a desired level of sympathetic nerve activity is exceeded, nerves proximate the probe are ablated at 1114, such as using an radio frequency or microwave ablation element comprising a part of the probe located between the sense electrode and the stimulation electrode, as shown in FIGS. 5 and 6. Steps 1108-1112 are then repeated and the nerve is optionally ablated again, until the sympathetic nerve activity is determined not to exceed the desired level at 1112. At that point, the measurement and nerve ablation is complete, and the probe and sheath can be withdrawn at 1116.

Although the examples presented here primarily illustrate measurement of sympathetic nerve activity using the probe systems described, probe system such as those illustrated here can also be used to monitor organ activity, pain, or other nervous system indicia. For example, pain can be monitored during surgery in some applications, or nerve activity can be measured while externally stimulating an organ.

Although specific embodiments have been illustrated and described herein, any arrangement that achieve the same purpose, structure, or function may be substituted for the specific embodiments shown. This application is intended to cover any adaptations or variations of the example embodiments of the invention described herein. These and other embodiments are within the scope of the following claims and their equivalents.

The invention claimed is:

1. An intraluminal microneurography probe, comprising:
   a probe body that is substantially cylindrical and having a diameter and a length that is perpendicular to the diameter, the probe body configured to be introduced into a blood vessel near an organ of a body without preventing blood flow through the blood vessel: and
   an expandable sense electrode configured to expand from the probe body toward a wall of the blood vessel when introduced, wherein the expandable sense electrode comprises an expandable wire helix that provides a continuously electrically exposed mesh of wires that expands to form a continuous conductive outer circumference to permit an entire outer circumference of the expandable sense electrode to provide circumferential electrical contact with the wall of the blood vessel; and
   an expandable stimulation electrode configured to expand from the probe body toward the wall of the blood vessel when introduced, wherein the expandable stimulation electrode comprises an expandable wire helix that provides a continuously electrically exposed mesh of wires that expands to form a continuous conductive outer circumference to permit an entire outer circumference of the expandable stimulation electrode to provide circumferential electrical contact with the wall of the blood vessel,
   wherein the expandable sense electrode and the expandable stimulation electrode are substantially distanced apart to enable the expandable sense electrode to be used to accurately detect a typical nerve action potential without interference from the expandable stimulation electrode.

2. The intraluminal microneurography probe of claim 1, wherein the expandable sense electrode is fixed to the probe body at a first end of the expandable sense electrode and movable relative to the probe body at a second end of the expandable sense electrode such that movement of the second end toward the first end causes the expandable sense electrode to expand.

3. The intraluminal microneurography probe of claim 1, further comprising:
   a first ground electrode configured to couple to the probe body; and
   a set of electrical connections operable to electrically couple at least the expandable sense electrode, the expandable stimulation electrode, and the first ground electrode to electrical circuitry.

4. The intraluminal microneurography probe of claim 3, wherein the expandable stimulation electrode is fixed to the probe body at a first end of the expandable stimulation electrode and movable relative to the probe body at a second end of the expandable stimulation electrode such that movement of the second end toward the first end causes the expandable sense electrode to expand.

5. The intraluminal microneurography probe of claim 3, wherein the first ground electrode is on or near the probe body.

6. The intraluminal microneurography probe of claim 5, further comprising a second ground electrode such that separate sense ground and stimulation ground electrodes are provided.

7. The intraluminal microneurography probe of claim 1, wherein the diameter of the probe body is 2 mm or less.

8. The intraluminal microneurography probe of claim 1, wherein the blood vessel is a renal artery.

9. The intraluminal microneurography probe of claim 1, wherein each wire of the continuously electrically exposed mesh of wires has a diameter of 8 to 10 thousandths of an inch.

10. The intraluminal microneurography probe of claim 1, wherein the expandable sense electrode and the expandable stimulation electrode are about 3 cm apart.

11. An intraluminal microneurography system, comprising:
   an intraluminal microneurography probe, comprising:
      a probe body configured to be introduced into a blood vessel without preventing blood flow through the blood vessel;
      an expandable stimulation electrode configured to expand from the probe body toward a wall of the blood vessel when introduced; and
      an expandable sense electrode configured to expand from the probe body toward the wall of the blood vessel when introduced;
   a first ground electrode;
   a second ground electrode;
   a stimulation circuit electrically coupled to the expandable stimulation electrode and the first ground electrode, the stimulation circuit configured to deliver one or more stimulation pulses with reference to the first ground electrode;
   a sense circuit electrically coupled to the expandable sense electrode and the second ground electrode, the sense circuit configured to sense nerve response signals with reference to the second ground electrode; and
   a filter coupled between the first ground electrode and the second ground electrode.

12. The intraluminal microneurography system of claim 11, further comprising a sheath operable to guide the probe into position within the blood vessel.

13. The intraluminal microneurography system of claim 12, wherein the first ground electrode is coupled to the sheath.

14. The intraluminal microneurography system of claim 12, wherein the second ground electrode is coupled to the probe body.

15. The intraluminal microneurography system of claim 12, wherein the first ground electrode is coupled to the sheath and the second ground electrode is coupled to the probe body; and the filter is a low-pass filter.

16. The intraluminal microneurography system of claim 11, wherein the filter, which is coupled between the first ground electrode and the second ground electrode, has a frequency response selected such that the second ground electrode does not drift significantly from the first ground electrode.

17. The intraluminal microneurography system of claim 11, wherein the filter, which is coupled between the first ground electrode and the second ground electrode, has a time constant selected such that the second ground electrode does not drift significantly from the first ground electrode.

18. The intraluminal microneurography system of claim 11, wherein the expandable sense electrode comprises:
   a wire having a diameter less than 15 thousandths of an inch, or a mesh of wires, each wire of the mesh of wires having a diameter less than 15 thousandths of an inch.

19. An intraluminal microneurography probe, comprising:
   a probe body that is substantially cylindrical and having a diameter and a length that is perpendicular to the diameter, the probe body configured to be introduced into a blood vessel near an organ of a body without preventing blood flow through the blood vessel;
   an expandable sense electrode configured to expand from the probe body toward a wall of the blood vessel when introduced, wherein the expandable sense electrode comprises an expandable wire helix that provides a continuously electrically exposed mesh of wires that expands to form a continuous conductive outer circumference to permit an entire outer circumference of the expandable sense electrode to provide circumferential electrical contact with the wall of the blood vessel;
   a neural ablation element attached to the probe body; and
   an expandable stimulation electrode configured to expand from the probe body toward the wall of the blood vessel when introduced, wherein the expandable stimulation electrode comprises an expandable wire helix that provides a continuously electrically exposed mesh of wires that expands to form a continuous conductive outer circumference to permit an entire outer circumference of the expandable stimulation electrode to provide circumferential electrical contact with the wall of the blood vessel,
   wherein the expandable sense electrode and the expandable stimulation electrode are substantially distanced apart to enable the expandable sense electrode to be used to accurately detect a typical nerve action potential without interference from the expandable stimulation electrode.

20. The intraluminal microneurography probe of claim 19 further comprising:
   a ground electrode configured to couple to the probe body; and
   a set of electrical connections operable to electrically couple at least the expandable sense electrode, the expandable stimulation electrode, the neural ablation element, and the ground electrode to electrical circuitry.

21. The intraluminal microneurography probe of claim 19, wherein the neural ablation element is attached to the probe body at a location between the expandable sense electrode and the expandable stimulation electrode.

22. The intraluminal microneurography probe of claim 19, wherein the neural ablation element includes a radio frequency ablation element.

23. The intraluminal microneurography probe of claim 22, further comprising a reflector configured to direct energy from the radio frequency ablation element in a specific direction.

24. The intraluminal microneurography probe of claim 19, wherein the neural ablation element comprises a microwave frequency ablation element.

25. The intraluminal microneurography probe of claim 19, further comprising a liquid cooling element configured to cool the neural ablation element.

26. The intraluminal microneurography probe of claim 25, wherein the liquid cooling element comprises a liquid jacket through which cooling liquid is pumped.

27. The intraluminal microneurography probe of claim 19, wherein each wire of the continuously electrically exposed mesh of wires has a diameter of less than 8 thousandths of an inch.

28. The intraluminal microneurography probe of claim 19, wherein the expandable sense electrode and the expandable stimulation electrode are about 3 cm apart.

* * * * *